(12) United States Patent
Ghosh et al.

(10) Patent No.: US 9,950,176 B2
(45) Date of Patent: *Apr. 24, 2018

(54) MODIFYING ATRIOVENTRICULAR DELAY BASED ON ACTIVATION TIMES

(71) Applicant: Medtronic, Inc., Minneapolis, MN (US)

(72) Inventors: Subham Ghosh, Blaine, MN (US); Robert W. Stadler, Shoreview, MN (US)

(73) Assignee: MEDTRONIC, INC., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/668,945

(22) Filed: Aug. 4, 2017

(65) Prior Publication Data

US 2017/0326368 A1 Nov. 16, 2017

Related U.S. Application Data

(63) Continuation of application No. 15/176,958, filed on Jun. 8, 2016, now Pat. No. 9,757,567, which is a continuation of application No. 13/744,038, filed on Jan. 17, 2013, now Pat. No. 9,381,362.

(60) Provisional application No. 61/588,924, filed on Jan. 20, 2012.

(51) Int. Cl.
*A61N 1/362* (2006.01)
*A61N 1/368* (2006.01)
*A61N 1/365* (2006.01)

(52) U.S. Cl.
CPC ......... *A61N 1/3682* (2013.01); *A61N 1/3622* (2013.01); *A61N 1/3684* (2013.01); *A61N 1/36514* (2013.01); *A61N 1/36592* (2013.01)

(58) Field of Classification Search
CPC .............................. A61N 1/3682; A61N 1/3684
See application file for complete search history.

(56) References Cited

U.S. PATENT DOCUMENTS

| | | | |
|---|---|---|---|
| 3,704,681 A | 12/1972 | Campbell et al. |
| 4,704,681 A | 11/1987 | Shimizu et al. |
| 5,048,535 A | 9/1991 | Maruyama |
| 5,697,378 A | 12/1997 | Elghazzawi |
| 7,283,872 B2 | 10/2007 | Boute et al. |

(Continued)

FOREIGN PATENT DOCUMENTS

| | | |
|---|---|---|
| CN | 101102811 | 1/2008 |
| CN | 1015411376 | 9/2009 |

(Continued)

OTHER PUBLICATIONS

(PCT/US2013/022123) PCT Notification of Transmittal of the International Search Report and the Written Opinion of the International Searching Authority, dated Apr. 26, 2013, 14 pages.

*Primary Examiner* — George Evanisko
(74) *Attorney, Agent, or Firm* — Mueting, Raasch & Gebhardt, P.A.

(57) ABSTRACT

Methods and/or devices may be configured to monitor ventricular activation times and modify an atrioventricular delay (AV delay) based on the monitored ventricular activation times. Further, the methods and/or devices may determine whether the AV delay should be modified based on the measured activation times before modifying the AV delay.

20 Claims, 7 Drawing Sheets

(56) References Cited

U.S. PATENT DOCUMENTS

| | | | |
|---|---|---|---|
| 7,590,446 B1* | 9/2009 | Min | A61N 1/368 607/9 |
| 7,702,390 B1 | 4/2010 | Min | |
| 7,706,879 B2 | 4/2010 | Burnes et al. | |
| 9,381,362 B2* | 7/2016 | Ghosh | A61N 1/36592 |
| 9,757,567 B2 | 9/2017 | Ghosh et al. | |
| 2007/0129762 A1 | 6/2007 | Worley | |
| 2009/0112108 A1 | 4/2009 | Nelson et al. | |
| 2010/0023079 A1 | 1/2010 | Hettrick et al. | |
| 2010/0030295 A1 | 2/2010 | Whinnett et al. | |
| 2010/0145405 A1 | 6/2010 | Min et al. | |
| 2011/0004264 A1 | 1/2011 | Siejko et al. | |

FOREIGN PATENT DOCUMENTS

| | | |
|---|---|---|
| CN | 102119045 | 7/2011 |
| WO | WO 02/40097 A1 | 5/2002 |

* cited by examiner

MODIFYING ATRIOVENTRICULAR DELAY BASED ON ACTIVATION TIMES

CROSS-REFERENCE TO RELATED APPLICATION

This application is a continuation of U.S. patent application Ser. No. 15/176,958, filed Jun. 8, 2016 entitled "MODIFYING ATRIOVENTRICULAR DELAY BASED ON ACTIVATION TIMES," which is a continuation of U.S. Pat. No. 9,381,362, issued Jul. 5, 2016 entitled "MODIFYING ATRIOVENTRICULAR DELAY BASED ON ACTIVATION TIMES," which claims the benefit of U.S. Provisional Patent Application Ser. No. 61/588,924 filed 20 Jan. 2012, entitled "MODIFYING ATRIOVENTRICULAR DELAY BASED ON ACTIVATION TIMES," which are all incorporated herein by reference in their entirety.

BACKGROUND

The disclosure herein relates to methods and devices for modifying atrioventricular delays based on activation times within cardiac tissue to, e.g., maintain effective pacing therapy.

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers causing a depolarization and the resulting atrial chamber contractions. The excitation pulse is further transmitted to and through the ventricles via the atrioventricular (AV) node and a ventricular conduction system causing a depolarization and the resulting ventricular chamber contractions.

Disruption of this natural pacemaking and conduction system as a result of aging or disease can be treated by artificial cardiac pacing. For example, one or more heart chambers may be electrically paced depending on the location and severity of the conduction disorder. In addition, cardiac pacing for ventricular dyschrony, often referred to as cardiac resynchronization therapy (CRT), may include pacing one or both ventricles before normal conduction through the AV node depolarizes the ventricles.

Implantable medical devices (IMDs) are capable of utilizing pacing therapies, such as CRT, to maintain hemodynamic benefits to patients. Pacing therapy may be delivered from an implantable generator, through a lead, and into the patient's heart. Basic programmable pacing parameters include atrioventricular delay (AV delay), left ventricle to right ventricle delay (VV delay), pacing amplitude, pacing rate, pulse duration, and pacing pathway or vector (e.g., bipolar such as a lead tip electrode to a lead ring electrode, etc. or unipolar such as a lead tip electrode to IMD casing, or housing), which all may be configured to ensure effective therapy to the patient.

For some patients suffering from heart failure and intraventricular conduction delays due to, e.g., left bundle branch block, right bundle branch block, the delivery of CRT can occur due to a single ventricular pacing stimulus by pre-exciting the ventricle with conduction delay. Such a stimulus must be properly timed relative to intrinsic depolarization of the other, non-delayed ventricle. This phenomenon may be referred to herein as "fusion pacing" since ventricular activation from a pacing stimulus fuses or merges with ventricular activation from intrinsic conduction. When the ventricular pacing stimulus is properly timed a desired ventricular resynchronization results with a minimum of pacing energy, thereby extending the operating life of an implantable pulse generator (e.g., an implantable cardioverter-defibrillator, pacemaker, and the like). Moreover, in some cases a more effective or physiologic form of CRT delivery can be achieved since the system and methods herein utilize a portion of intrinsic activation, which can be superior to an entirely evoked (e.g., paced) form of CRT. Fusion pacing may also be referred to herein as left ventricle-only pacing or right ventricle-only pacing.

One method of fusion pacing, or left ventricle-only pacing, includes pacing the left ventricle at an appropriate time to achieve fusion of a paced wavefront with an intrinsic depolarization of the right ventricle. One method of fusion pacing, or right ventricle-only pacing, includes pacing the right ventricle at an appropriate time to achieve fusion of a paced wavefront with an intrinsic depolarization of the left ventricle. Such a CRT method may reduce device power output relative to biventricular pacing and may improve hemodynamics, especially at lower heart rates.

One specific parameter that may be used by an IMD to deliver cardiac therapy (e.g., CRT such as left ventricular fusion pacing) is an atrioventricular delay (AV delay), which may generally be described as a programmable value representing a time period between atrial electrical activity, whether intrinsic (e.g., natural) or paced, and the delivery of ventricular pacing. The optimal value of the AV delay has generally been defined as a delay that produces the maximum stroke volume for a fixed heart rate or the maximum cardiac output for a sinus node driven heart rate.

To optimize or adjust the AV delay, a cardiac therapy device such as an IMD may measure a patient's intrinsic AV conduction time. A patient's intrinsic AV conduction time is the time between an intrinsic atrial event (e.g., depolarization of the right atrium) and an intrinsic ventricular event (e.g., depolarization of the right ventricle). As used herein, an "intrinsic" event or conduction is one that occurs or is conducted naturally (e.g., an intrinsic ventricular event is an event triggered by electrical activity transmitted across the AV node of the heart from the atria to the ventricles, etc.). A cardiac therapy device may periodically measure a patient's intrinsic AV conduction time, or interval, and adjust the AV delay in response to the measured intrinsic AV conduction time, e.g., to optimize cardiac functionality.

For example, a CRT algorithm (e.g., performed by an IMD) may measure a patients intrinsic AV conduction time once every minute by forcing delays used for ventricular pacing (e.g., paced AV delay, sensed AV delay, etc.) to long values (e.g., 300 milliseconds (ms), 350 ms, etc.). Conventionally, the intrinsic AV conduction time measurement has been performed periodically (e.g., every 60 seconds) so that the CRT algorithm can adapt to changes in the patient's intrinsic AV conduction time.

In other words, CRT algorithms may temporarily suspend, or interrupt, pacing therapy for one or more heartbeats to measure a patient's intrinsic AV conduction time for use in modifying or adjusting (e.g., optimizing) one or more pacing parameters such as AV delay.

SUMMARY

One exemplary implantable medical device operable for delivery of cardiac therapy to a patient includes a therapy delivery module, a sensing module, and a control module coupled to the therapy delivery module and to the sensing module. The therapy delivery module may be configured to deliver pacing therapy to either the left ventricle or the right ventricle of a patient's heart using at least one electrode. The sensing module may be configured to sense electrical activity of the patient's heart (e.g., electrical activity of the right or left ventricle, far-field electrical activity of the right or left ventricle, near-field electrical activity of the right or left ventricle, etc.) using at least one electrode. The control module may be configured to control the delivery of pacing therapy to either the left ventricle or the right ventricle of a patient's heart based on an AV delay (where the pacing therapy is delivered over a plurality of heartbeats) and sense electrical activity of the patient's heart using the sensing module during the delivery of the pacing therapy. The control module may be further configured to measure a ventricular activation time for each of the plurality of heartbeats between the delivery of pacing stimulus of the pacing therapy and at least one selected fiducial point of the sensed electrical activity (e.g., a maximum negative slope of the far-field electrical activity of the right ventricle of the patient's heart, a maximum value of the near-field electrical activity of the right ventricle of the patient's heart, etc.) resulting from at least one of the delivered pacing stimulus of the pacing therapy and an intrinsic conduction of the patient's heart. The control module may be further configured to modify the AV delay for use in delivering pacing therapy based on the measured ventricular activation times if one or more of the measured ventricular activation times are greater than or less than a predetermined reference activation time by a selected threshold value (e.g., if a first selected number of the measured ventricular activation times are greater than or less than the predetermined reference activation time by the selected threshold value over a second selected number of heartbeats).

One exemplary method for use in an implantable medical device operable for delivery of cardiac therapy to a patient includes delivering pacing therapy to either the left ventricle or the right ventricle of a patient's heart using at least one electrode based on an AV delay using an implantable medical device (e.g., where the pacing therapy is delivered over a plurality of heartbeats) and sensing electrical activity of the patients heart (e.g., electrical activity of the right or left ventricle, far-field electrical activity of the right or left ventricle, near-field electrical activity of the right or left ventricle, etc.) using at least one electrode of the implantable medical device during the delivery of the pacing therapy. The exemplary method may further include measuring a ventricular activation time for each of the plurality of heartbeats between the delivery of pacing stimulus of the pacing therapy and at least one selected fiducial point of the sensed electrical activity (e.g., a maximum negative slope of the far-field electrical activity of the right, ventricle of the patient's heart, a maximum value of the near-field electrical activity of the right ventricle of the patient's heart, etc.) resulting from at least one of the delivered pacing stimulus of the pacing therapy and an intrinsic conduction of the patient's heart. The exemplary method may further include modifying the AV delay for use in delivering pacing therapy based on the measured ventricular activation times if one or more of the measured ventricular activation times are greater than or less than a predetermined reference activation time by a selected threshold value (e.g., if a first selected number of the measured ventricular activation times are greater than or less than the predetermined reference activation time by the selected threshold value over a second selected number of heartbeats).

In one or more exemplary devices and methods, modifying the AV delay for use in delivering pacing therapy based on the measured ventricular activation times may include setting the AV delay to the last AV delay plus the last measured ventricular activation time minus the predetermined reference activation time or selling the AV delay to either a mode or a median of a selected number of previous AV delays plus either a mode or median of the selected number of ventricular activation time differences. The ventricular activation time differences may be the measured ventricular activation times minus the predetermined reference activation time.

In one or more exemplary devices and methods, modifying the AV delay for use in delivering pacing therapy based on the measured ventricular activation times may include modifying the AV delay for use in delivering pacing therapy if a standard deviation of a first selected number of the activation time differences are less than a selected variability threshold value over a second selected number of heartbeats, wherein the ventricular activation time differences are the measured ventricular activation times minus the predetermined reference activation time.

In one or more exemplary methods and devices, the exemplary methods may further include and the control module of the exemplary devices may be further configured to execute delivering biventricular pacing therapy to the patient's heart using the implantable medical device if the modified AV delay is greater than a selected limit value.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-7. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Generally, diagnostic methods and devices that can perform a beat-to-beat adjustment or modification of an AV delay, without interruption of pacing therapy, are described herein. For example, exemplary devices and methods described herein relate to monitoring one or more ventricular activation times (e.g., right ventricular activation times and/or left ventricular activation times) and modifying or adjusting the AV delay based on the monitored ventricular activation times. More specifically, in one or more embodiments, exemplary devices and methods may monitor ventricular activation times between the delivery of pacing stimulus to one of either the left ventricle or right ventricle using at least one pacing electrode and the sensing of electrical activity (e.g., depolarization) in the opposite ventricle using one or more sensing electrodes resulting either from the pacing stimulus or an intrinsic conduction. These monitored ventricular activation times may be used to adjust, or modify, the AV delay (e.g., used to determine when to deliver left or right ventricular pacing) to, e.g., maintain effective pacing therapy.

One or more exemplary methods and devices described herein may provide frequent adjustment of left ventricular (LV) pace timing without periodic withholding of pacing therapy (e.g., CRT) to measure a patient's intrinsic AV conduction time. In at least one embodiment, a far-field or near-field right ventricular electrogram (EGM) may be monitored close to the timing of a LV pace. For the far-field EGM, the peak negative slope of the EGM may indicate local right ventricular (RV) activation. For the near-field EGM, the absolute peak EGM amplitude may indicate local RV activation. The timing of the local RV activation relative to the delivery of the LV pace, which is the measured right ventricular activation time, may be used to adjust future LV pacing timing (e.g., the AV delay).

Further, one or more exemplary methods and devices described herein may allow for more frequent assessment of the need for adjustments to AV delay for LV-only pacing without withholding or interrupting CRT pacing. More frequent adjustments of AV delay may lead to more robust fusion pacing and improved CRT response. Further, the exemplary methods and devices may also avoid inappropriate changes in timing of LV-only pacing due to ectopy or premature beats.

Figure 1:
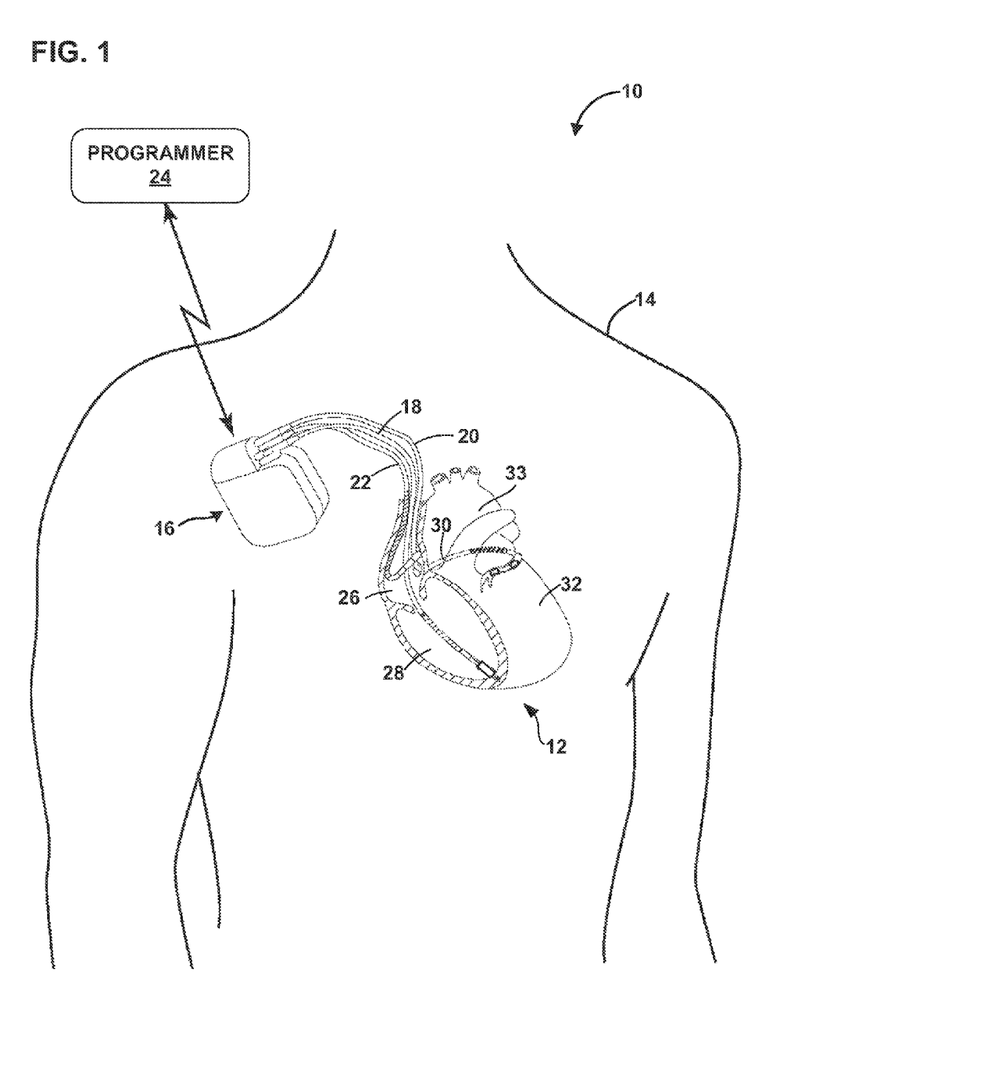
FIG. 1 is a diagram of an exemplary system including an exemplary implantable medical device (IMD).

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and/or a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 10, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more measured ventricular activation times and/or one or more pacing parameters such as AV delay (or, e.g., VV delay, modulation of multisite pacing such as pacing from more than one site in the LV or RV, etc.). The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
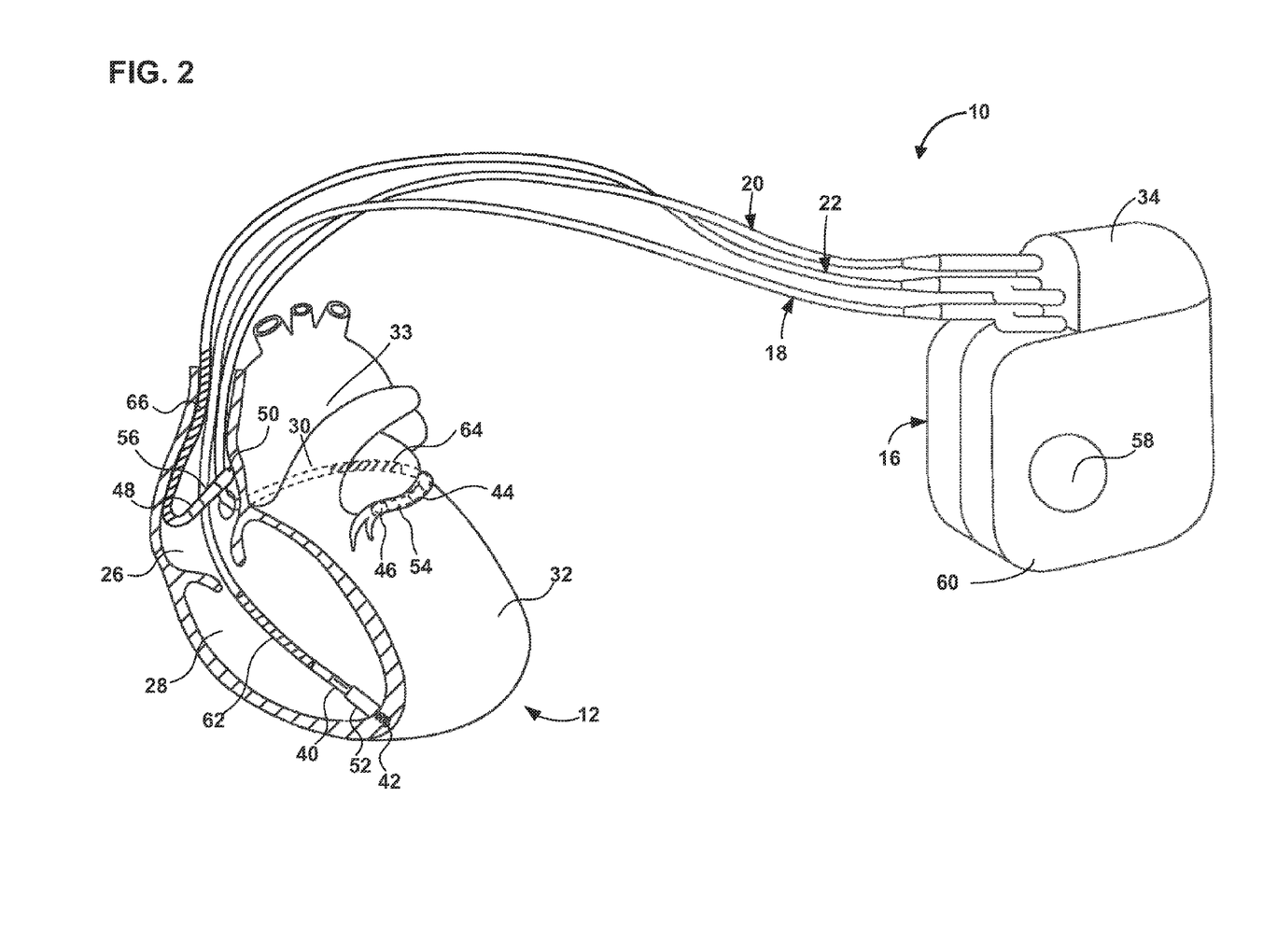
FIG. 2 is a diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48 and 50 may be used for unipolar sensing or pacing in combination with housing electrode 58. Further, any of electrodes 40, 42, 44, 48, 48, 50, 58, which are not being used to deliver pacing therapy, may be used to sense electrical activity during pacing therapy (e.g., for use in determining activation times). As described in further detail with reference to FIG. 3, the housing 60 may enclose a therapy delivery module that may include a stimulation generator for generating cardiac pacing pulses and defibrillation or cardioversion shocks, as well as a sensing module for monitoring the patient's heart rhythm.

The leads 18, 20, 22 may also include elongated electrodes 62, 64, 86, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in determining activation times). In at least one embodiment, the LV elongated electrode 64 may be used to sense electrical activity of a patient's heart during the deliver of pacing therapy.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3:
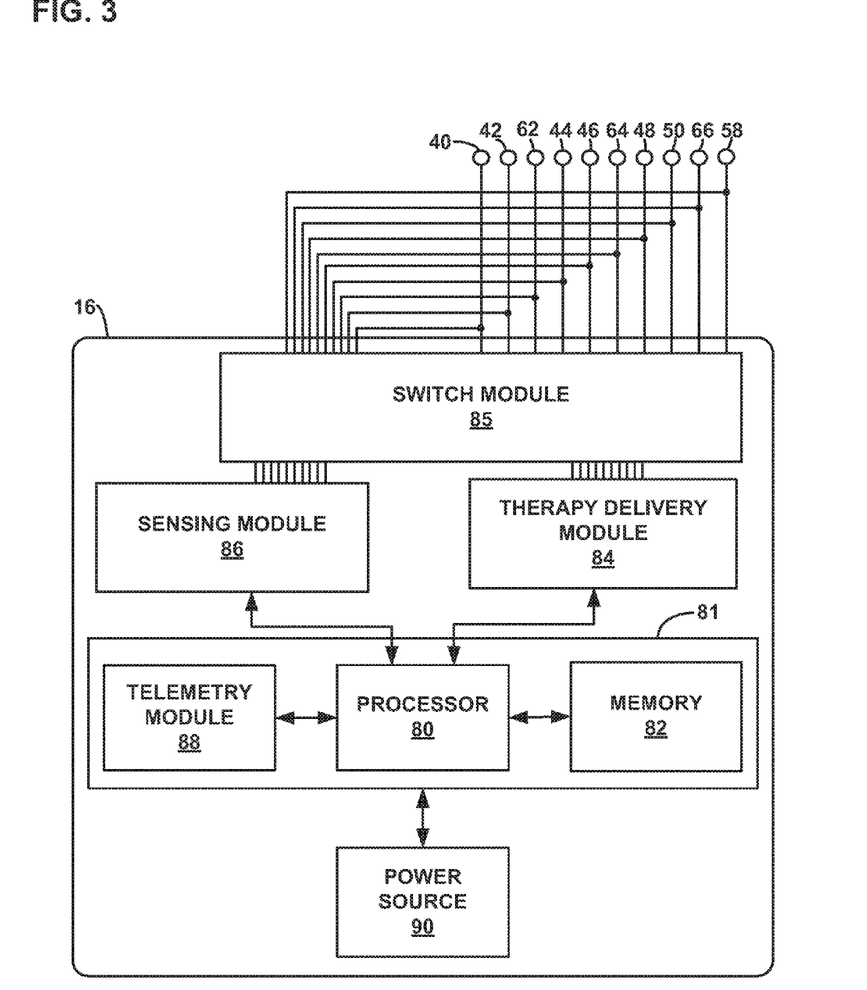
FIG. 3 is a block diagram of an exemplary IMD, e.g., the IMD of FIGS. 1-2.

FIG. 3 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor BO may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 18. Therapy delivery module 84 may be configured to generate and deliver electrical stimulation therapy such as pacing therapy to the heart 12 using one or more of the electrodes 40, 42, 44, 48, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 88 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart. In some examples, the control module 81 may select the electrodes that function as sensing electrodes via the switch module within the sensing module 86, e.g., by providing signals via a data/address bus. In some examples, the sensing module 88 may include one or more sensing channels, each of which may include an amplifier.

Signals from the selected sensing electrodes may be provided to a multiplexer, and thereafter converted to multibit digital signals by an analog-to-digital converter for storage in memory 82, e.g., as an electrogram (EGM). In some examples, the storage of such EGMs in memory 82 may be under the control of a direct memory access circuit. The control module 81 (e.g., using the processor 80) may employ digital signal analysis techniques to analyze the digitized signals stored in memory 82 to detect and measure, e.g., ventricular activation times within the EGMs. For example, the processor 80 may be configured to measure activation times of cardiac tissue using EGMs from one or more electrodes in contact, or in proximity, with cardiac tissue by employing any of the numerous signal processing methodologies known in the art.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing, in the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 48, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be unlinked to the programmer 24 and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Generally, one or more parameters of CRT (e.g., pacing parameters) may be adjusted, or modified, based on one or more sensed physiological signals, etc., to, e.g., deliver effective cardiac therapy to a patient. One parameter of CRT that may be adjusted is an AV delay, which may be used to determine when to deliver ventricular pacing based on either sensed intrinsic atrial activity or paced atrial activity. Often, the AV delay may be adjusted based on a measurement of a patient's intrinsic AV conduction time. To measure a patient's intrinsic AV conduction time, CRT methods and devices may temporarily suspend pacing therapy for one or more heartbeats such that the natural depolarization of the patient's heart may be monitored.

The exemplary methods and devices described herein may adjust the AV delay without temporarily suspending pacing therapy by using ventricular activation times monitored during pacing therapy. For example, ventricular activation times may be associated, or correlated, with optimal timings for the delivery of ventricular pacing (e.g., LV-only pacing, RV-only pacing, biventricular pacing, etc.), and thus, ventricular activation times monitored during pacing therapy may be used to adjust one or more pacing parameters such as, e.g., AV delay (which is used to determine when to deliver ventricular pacing).

Measurement of activation times can be performed by picking an appropriate fiducial point (e.g., peak or maximum values, trough or minimum values, minimum positive or negative slopes, maximum positive or negative slopes, zero crossings, threshold crossings, etc. of a near or far-field electrograms) and measuring a time period between the delivery of pacing stimulus using a pacing electrode and the appropriate fiducial point within the electrical activity (e.g., EGM) sensed by a non-pacing electrode. In other words, activation times between a pacing electrode and a non-pacing electrode distant from the pacing electrode may be measured by picking, or selecting, an appropriate point within the EGM recorded by the non-pacing electrode during pacing therapy (e.g., biventricular stimulation, LV-only pacing, RV-only pacing, etc.) with respect to the pacing spike. Exemplary activation times shown within different waveforms, or EGMs, will be further described herein with respect to FIG. 4.

Figure 4:
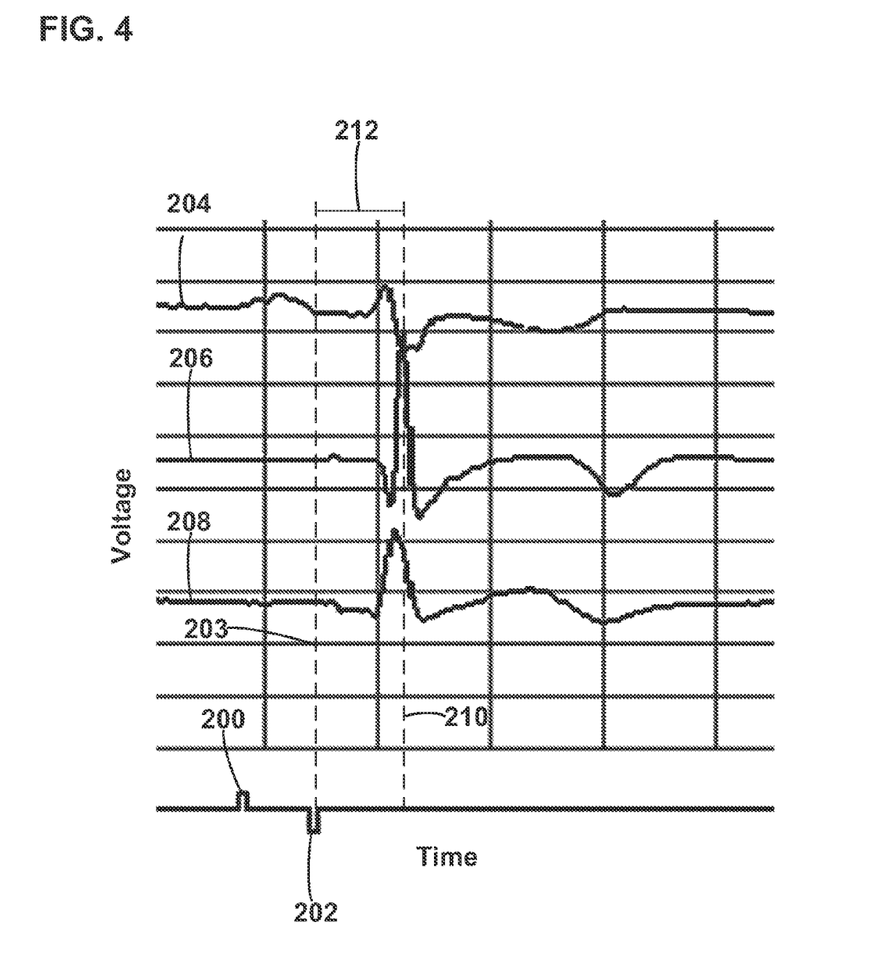
FIG. 4 is a graph depicting electrograms of different sensing vectors for use in measuring right ventricular activation time.

Three electrograms 204, 206, 208, an atrial sense 200, and a left ventricular pace 202 are depicted over time in FIG. 4. The electrogram 204 is a general purpose electrocardiogram recorded from an external electrode, the electrogram 206 is a bipolar, near-field electrogram using a RV tip electrode and RV ring electrode to capture near-field RV activity, and the electrogram 208 is a unipolar, far-field electrogram using a RV tip electrode and, e.g., a can or housing electrode, to capture far-field RV activity.

The peak value of the near-field electrogram 208 and the maximum negative slope of the far-field electrogram 208 are indicative of right ventricular activation (as shown by the dashed line 210 extending therethrough). Thus, a RV activation time 212 may be measured between the left ventricular pace 202 and one or both of the peak value of the near-field electrogram 206 and the maximum negative slope of the far-field electrogram 208.

The exemplary methods and/or devices described herein may track, or monitor, ventricular activation times (e.g., right ventricular activation time, left ventricular activation time, etc.) and adjust one or more pacing parameters such as AV delay based on the monitored activation times. One manifestation of the basic flow can be seen in exemplary method 100 of FIG. 5. Exemplary method 100 includes various processes to measure ventricular activation times and to modify AV delays for use in delivering pacing therapy based on the measured ventricular activation times. Exemplary method 100 is intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

Figure 5:
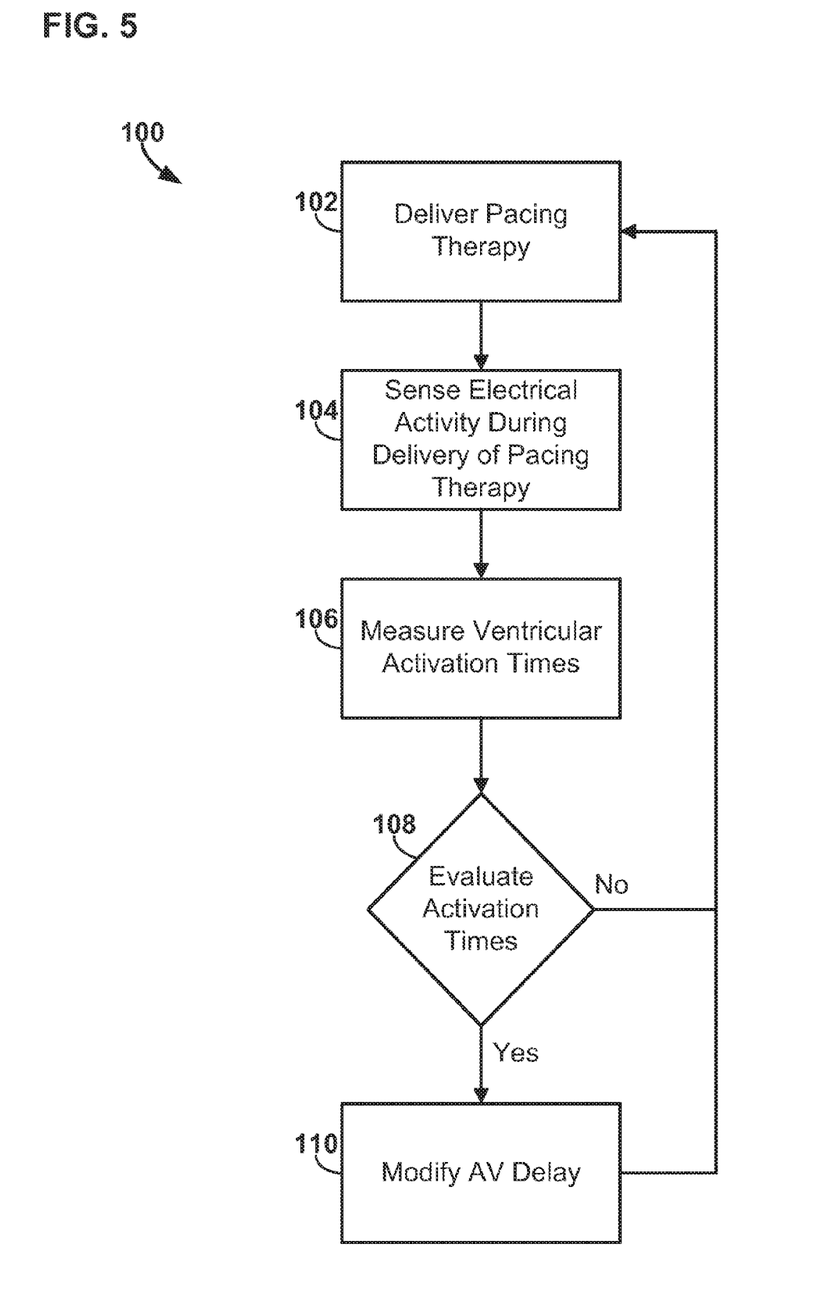
FIG. 5 is a general flow chart of an exemplary method of modifying atrioventricular delay (AV delay) based on ventricular activation times, e.g., using the IMDs of FIGS. 1-3.

The exemplary method 100 of FIG. 5 includes delivering pacing therapy 102 (e.g., using the IMD 16 described herein). Delivering pacing therapy 102 may include monitoring a patient's heart and delivering electrical pacing pulses to the patient's heart, e.g., to maintain the patient's heartbeat (e.g., to regulate a patient's heartbeat, to improve and/or maintain a patient's hemodynamic efficiency, etc.). More specifically, the pacing therapy 102 may include LV-only pacing or RV-only pacing. In other words, pacing therapy may be delivered to either the left ventricle or the right ventricle of the patient's heart. As described herein, the delivery of pacing therapy may be based on one or more pacing parameters including an AV delay, which may be modified according to exemplary method 100.

During the delivery of pacing therapy 102, the pacing therapy 102 may become less effective due to, e.g., changes in the patient's physical activity, changes in cardiac tissue, changes in ventricular conduction velocity, changes in ventricular conduction patterns, changes in intrinsic conduction AV times, changes in heart rate, changes in sympathetic or parasympathetic stimulation, etc. To compensate for such changes, the exemplary method 100 may sense electrical activity of the patient's heart during the delivery of pacing therapy 104 with one or more electrodes not used to pace the patient's heart. For example, the electrical activity may be sensed 104, or monitored, using at least one sensing electrode during the delivery of pacing stimulus (e.g., pacing pulses) from one or more pacing electrodes such that the electrical activity which results from the pacing stimulus or an intrinsic conduction (e.g., whichever occurs first and results in a depolarization) may be sensed, or seen, in the electrogram of the at least one sensing electrode (e.g., unipolar or bipolar configurations).

More specifically, ventricular activation times may be measured 106 using the sensed electrical activity during the delivery of pacing therapy 104. In at least one embodiment, the pacing therapy may be LV-only pacing therapy, which includes pacing stimulus delivered to only the left ventricle of the patient's heart (and not the right ventricle). As such, the exemplary method delivering LV-only pacing therapy may measure the right ventricular activation time, which is the time between the delivery of pacing stimulus to the left ventricle and the depolarization of the right ventricle due to, e.g., an intrinsic conduction or the pacing stimulus delivered to the left ventricle and conducted to the right ventricle (e.g., whichever occurs first).

In at least another embodiment, the pacing therapy may be RV-only pacing therapy, which includes pacing stimulus delivered to only the right ventricle of the parent's heart (and not the left ventricle). As such, the exemplary method delivering RV-only pacing therapy may measure the left ventricular activation time, which is the time between the delivery of pacing stimulus to the right ventricle and the depolarization of the left ventricle due to, e.g., an intrinsic conduction or the pacing stimulus to the right ventricle (whichever occurs first).

The electrodes used to deliver pacing stimulus and sensing electrical activity for use in measuring activation times may be described in terms of a first electrode and a second electrode. For example, the pacing therapy may be delivered with at least a first electrode and the electrical activity may be sensed with at least a second electrode. The second electrode, or any other electrode configured to sense the electrical activity during the delivery of pacing stimulus, may not be a pacing electrode. In other words, the second electrode may not be configured for delivering pacing therapy. Further, the second, or sensing, electrode may be a pacing electrode that is simply not being used to deliver pacing therapy (e.g., not ever used for delivery of pacing therapy, not being used to deliver pacing therapy at the same time as the first electrode, etc.).

In the example of LV-only pacing therapy, the first electrode, or the pacing electrode, may be configured to pace the left ventricle of patient's heart and the second electrode, or the sensing electrode, may be configured to sense electrical activity of the right ventricle of patient's heart. In at least one LV-only pacing therapy embodiment, the pacing electrode, or first electrode, may be a LV tip electrode configured to pace the free wall of the left ventricle, and the sensing electrode, or second electrode, may be a RV ring electrode, a RV tip electrode, or a RV elongated (e.g., defibrillation) electrode. For example, a near-field right ventricular EGM may be measured, or sensed, between a RV tip electrode and a RV ring electrode. Further, for example, a far-field right ventricular EGM may be measured, or sensed, between a RV tip electrode and a can, or housing, electrode (e.g., electrode 58).

In the example of RV-only pacing therapy, the first electrode, or the pacing electrode, may be configured to pace the right ventricle of patient's heart and the second electrode, or the sensing electrode, may be configured to sense electrical activity of the left ventricle of patient's heart. In at least one RV-only pacing therapy embodiment, the pacing electrode, or first electrode, may be a RV tip electrode configured to pace the endocardial apical or septal wall of the right ventricle, and the sensing electrode, or second electrode, may be a LV ring electrode, a LV tip electrode, or a LV elongated (e.g., defibrillation) electrode. For example, a near-field left ventricular EGM may be measured, or sensed, between a LV tip electrode and a LV ring electrode. Further, for example, a far-field left ventricular EGM may be measured, or sensed, between a LV tip electrode and a can, or housing, electrode (e.g., electrode 58).

Further, the second electrode may be located a distance away from the first electrode (e.g., the pacing electrode) such that an activation time may be monitored. For example, if the first electrode and the second electrode were located too close to one another, an activation time may be too short for use in modifying one more pacing parameters such as, e.g., AV delay.

Since the exemplary method 100 may not use pacing electrodes to sense the electrical activity for use in modifying one or more pacing parameters such as AV delay, sensing 104 may take place for every paced beat (e.g., beat-to-beat, etc.) such that pacing therapy is not interrupted. As such, the ventricular activation time for each heartbeat of a plurality of heartbeats may be monitored using exemplary method 100 without interruption.

As described herein, ventricular activation times may be measured 106 using the electrical actively sensed 104 using one or more sensing electrodes. For example, a fiducial point on the waveform of the sensed electrical activity may be selected to be used with the exemplary method 100. The time between the delivery of the pacing therapy (e.g., to the LV, to the RV, etc.) and the selected fiducial point within the waveform of the sensed electrical activity resulting from either the pacing therapy (e.g., pacing stimulus) or an intrinsic activation is the measured ventricular activation time.

The fiducial point may be selected to be a characteristic of the sensed electrical activity resulting from (e.g., a product of) the pacing therapy or an intrinsic activation that is repeatedly, or consistently, recognizable such that ventricular activation times may be repeatedly, or consistently, measured. In at least one embodiment, the fiducial point may be a peak, or maximum, value in a near-field waveform, or electrogram, sensed by the sensing electrode (e.g., as shown by electrogram 206 shown in FIG. 4). In at least another embodiment, the fiducial point may be a peak, or maximum, negative slope value (e.g., the steepest negative slope) in a far-field waveform, or electrogram, sensed by the sensing electrode (e.g., as shown by electrogram 208 shown in FIG. 4). For example, a derivative function of the far-field electrogram may be calculated, or computed, to determine the peak, or maximum, negative slope value of the far-field electrogram.

Based on the measured activation times 106, the exemplary method 100 may modify an AV delay, e.g., which may be used in the delivery of pacing therapy, based on the measured activation times 108. As shown in FIG. 5, before the exemplary method 100 may modify the AV delay 110, the exemplary method 100 may evaluate one or more of the measured activation times 108 to determine whether the AV delay should be modified. For example, one or more measured activation time may be compared to a predetermined reference activation time indicative of effective, or optimal, pacing therapy. If the one or more activation times are greater than or less than the predetermined reference activation time by a selected threshold value, then exemplary method 100 may modify the AV delay.

The predetermined reference activation time may be defined as an optimal value of the ventricular activation time that produces a maximum stroke volume for a fixed heart rate or the maximum cardiac output for a sinus node driven heart rate or provides effective hemodynamic performance as measured by any number of invasive or noninvasive methods, including sensor-based measurements, narrowest QRS duration on the surface ECG, etc. In at least one embodiment, the predetermined reference activation time may be determined by a mapping function implemented within an implantable medical device which may determine the optimal value based on assessment of patient's intrinsic AV conduction at rest.

The predetermined reference activation time may be established by any number of methods. In at least one embodiment, a mean value representative of a plurality of monitored ventricular activation times, and its variability, may be evaluated for a selected number of beats (e.g., 60 heartbeats) during a post-implant follow-up at physician's office. A physician, or another practitioner, may visually monitor the pacing therapy using, e.g., an electrocardiogram of the patient's heart, to confirm that the pacing therapy is effective. Then, for example, the mean value (or any other statistic) of the monitored ventricular activation times may be calculated and used as the predetermined reference activation time indicative of effective pacing therapy. The variability may be used to calculate a threshold value, which is the difference torn the reference activation time that may be acceptable or allowable without indicating ineffective pacing therapy (which may initiate an AV delay adjustment).

In at least one embodiment, a reference activation time for LV-only pacing may be about 50 milliseconds (ms) and the threshold may be about 10 ms. In other words, in this embodiment, if the measured activation time is between about 40 ms (i.e., 50 ms minus 10 ms) and about 60 ms (i.e., 50 ms plus 10 ms), then the measured activation time may be determined to provide effective (e.g., optimal) pacing therapy, and thus, no modification of the AV delay should occur. Such values may be different for each patient and each different electrode combination used for pacing and sensing.

The predetermined reference activation time may be greater than or equal to about 30 ms, about 35 ms, about 40 ms, about 50 ms, about 55 ms, etc. Further, the predetermined reference activation time may be less than or equal to about 60 ms, about 65 ms, about 70 ms, about 80 ms, etc. The threshold value may be greater than or equal to about 2 ms, about 3 ms, about 5 ms, about 7 ms, etc. Further, the threshold value may be less than or equal to about 10 ms, about 12 ms, about 15 ms, 17 ms, etc.

In at least one embodiment, a single measured ventricular activation time may be evaluated 108 to initiate, or trigger, the modification of an AV delay 110. For example, if the last measured ventricular activation time is greater than or less than a predetermined reference activation time by a selected threshold value, then it may be determined 108 that the AV delay should be modified 110.

In other embodiments, more than one measured ventricular activation time may be evaluated 108 to initiate the modification of an AV delay 110. For example, if a first selected number (e.g., 5, 10, etc.) of consecutive measured ventricular activation times are greater than or less than a predetermined reference activation time by a selected threshold value over a second selected number (e.g., 10, 20, etc.) of heartbeats, then it may be determined that the AV delay should be modified 110. An exemplary method including a determination process based on more than one measured activation time to modify an AV delay is further described herein with reference to FIG. 6.

Still further, the standard deviation of one or more measured ventricular activation times may be compared to a selected variability threshold value to determine 108 if the AV delay should be modified 110. For example, if the standard deviation of a first selected number (e.g., 5) of the activation time differences (e.g., an activation time difference may be the measured ventricular activation time minus the predetermined reference activation time) are less than a selected variability threshold (e.g., 15 ms) over a second selected number of heartbeats (e.g., 10 heartbeats), then it may be determined that the AV delay should be modified 110. An exemplary method including a determination process based on the standard deviation of one or more measured ventricular activation times to modify an AV delay is further described herein with reference to FIG. 6.

Although standard deviation is used in this example to evaluate variability, any statistical metric may be used to evaluate the measured activation times. For example, the mean of absolute deviations of each activation time from the mean activation time may be used to evaluate the measured activation times.

If it is determined the AV delay should not be adjusted or modified, the exemplary method 100 may continue delivering pacing therapy 102, sensing electrical activity 104, measuring ventricular activation times 106, and evaluating the activation times 108 to determine whether AV delay or any other pacing parameter (e.g., VV delay, modulation of multisite pacing such as pacing from more than one site in the LV or RV, etc.) should be adjusted. If it is determined that AV delay should be adjusted or modified 108, the exemplary method 100 may advance to modifying the AV delay 110.

Generally, to modify the AV delay 110, the AV delay may be shortened or lengthened based upon the monitored ventricular activation times. For example, in LV-only pacing (e.g., in patients with left bundle branch block), if the ventricular activation times (e.g., the time period between the LV pace and the RV activation such as RV activation time 212 shown in FIG. 4) increase during subsequent fusion resynchronization pacing (e.g., RV activation occurs after LV pacing, moving toward a right bundle branch block pattern of activation, as shown in example 310 of FIG. 7 further described below), the AV delay for the LV pacing may be lengthened, or adjusted to longer values, to maintain ideal fusion. Conversely, in LV-only pacing, if the ventricular activation times subsequently decrease or become negative (e.g., RV activation occurs before LV pacing, moving toward a left bundle branch block pattern of activation, as shown in example 320 of FIG. 7 further described below), the AV delay for pacing may be shortened, or adjusted to shorter values, to maintain ideal fusion.

Further, when modifying the AV delay 110, either the last used AV delay or one or more statistical variations of one or more previously used AV delays may be used as a starting point for modification. In at least one embodiment, the AV delay may be set to the last used AV delay plus the last measured activation time minus the predetermined reference activation time.

In one or more embodiments, a mode, median, or average of a selected number of previous AV delays (e.g., the last five AV different delays, the AV delays used for the last 5 heartbeats, 10 heartbeats, 15 heartbeats, 20 heartbeats, etc.) may be used to modify the AV delay. For example, the AV delay may be set to one of a mode, a median, or average of a selected number (e.g., 5, 10 etc.) of previous AV delays plus one of a mode, a median, or average of the selected number of activation time differences. As described herein, an activation time difference may be the measured ventricular activation time minus the predetermined reference activation time.

Figure 6:
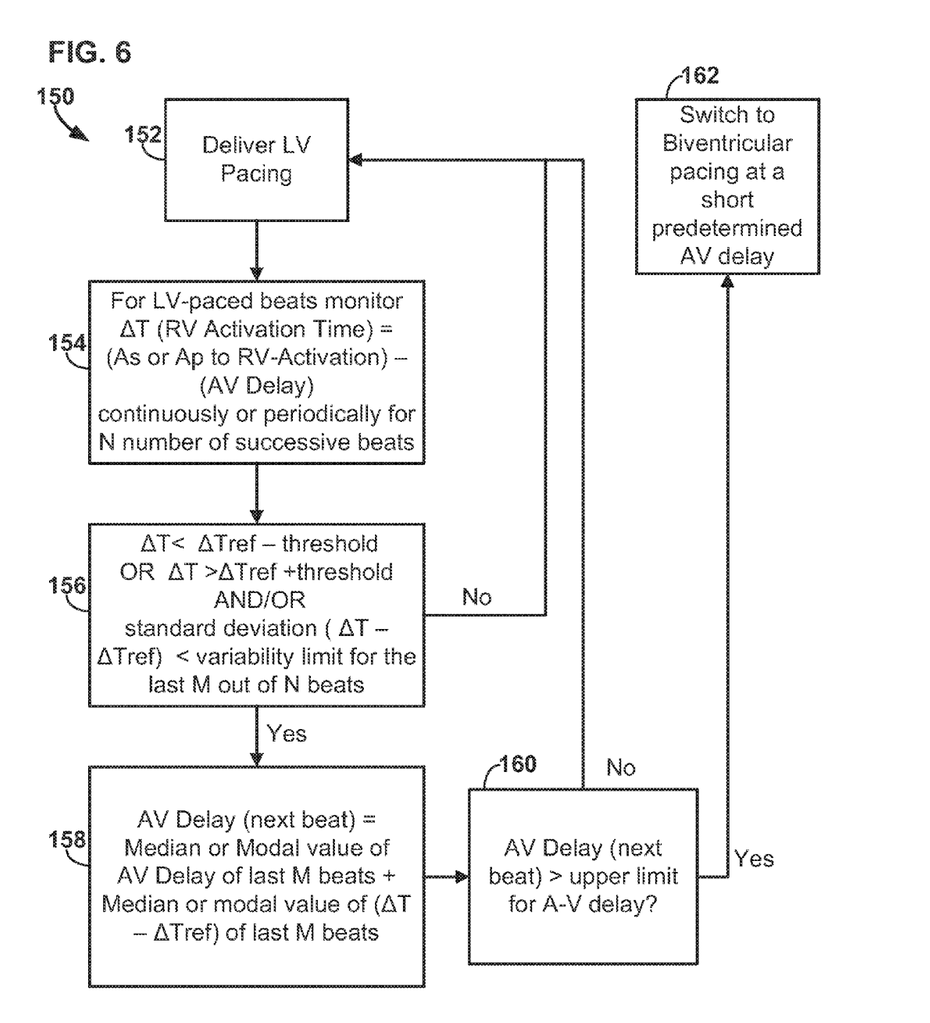
FIG. 6 is a flow chart of an exemplary method of modifying AV delay based on right ventricular activation times.

Another exemplary method 150 for use in modifying AV delay based on monitored ventricular activation times is depicted in FIG. 6. Exemplary method 150 is configured to deliver LV-only pacing therapy 152. As such, the ventricular activation times measured in exemplary method 150 are the right ventricular activation times since the left ventricle is being paced. In other words, the measured activation time is the time period between the delivery of a left ventricular pace and the depolarization of the right ventricle due to, e.g., either the pacing stimulus to the left ventricle or an intrinsic conduction.

For each paced heartbeat 152, a measured activation time, or $\Delta T$, may be measured and calculated continuously or periodically for a selected number of, or N, heartbeats 154 (e.g., 10 successive heartbeats). The measured activation time, or $\Delta T$, is equal to the time between an atrial sense or atrial pace and the right ventricular activation (e.g., as determined by analysis of an electrogram of the right ventricle) minus the AV delay (e.g., the time between either an atrial sense or atrial pace and the left ventricular pace).

The be measured activation times may then be evaluated 156. For example, if the measured activation time, or ΔT, is less than (e.g., less than or equal to) a predetermined reference activation time, or ΔTref, by a selected threshold value or is greater than (e.g., greater than or equal to) the predetermined reference activation time, or ΔTref, by the selected threshold, then it may be determined 158 that the AV delay should be adjusted 158.

As shown, the determination process 158 may also evaluate any statistical metric of the measured activation times such as, e.g., the standard deviation of the measured activation times from the predetermined reference activation times. For example, if a standard deviation of the difference between the measured activation time, or ΔT, and the predetermined reference activation time, or ΔTref, is less than a variability limit (e.g., 15 ms) for a first selected number of, or M, beats (e.g., 5 heartbeats) out a second selected number of, or N, beats (e.g., 10 heartbeats), then it may be determined 156 that the AV delay should be adjusted 158. If it is not determined that AV delay should be adjusted in process 156, the exemplary method 150 may continue delivering LV pacing 152 without adjusting the AV delay.

If it is determined that the AV delay should be adjusted, then the AV delay (e.g., the time period between the atrial sense or atrial pace and the ventricular pace) may be adjusted for the next beat 158. For example, the AV delay may be set to the median or modal value of the AV delay of a selected number of, or M, heartbeats (e.g., 5 heartbeats) plus a median or modal value of the difference between the measured activation times, or ΔT, and the predetermined reference activation time, or ΔTref, of the selected number of, or M, heartbeats 158.

After the AV delay has been adjusted 158, the exemplary method 150 may evaluate the newly adjusted AV delay 160 to, e.g., determine if the AV delay has been adjusted too far to deliver effective pacing therapy. For example, if the AV delay for pacing reaches an upper limit, the LV-only fusion pacing may be replaced by biventricular pacing at a short predetermined AV delay 162. The short predetermined AV delay may be about 80 ms to about 200 ms. If the AV delay has not exceeded a predetermined upper limit value, then exemplary method 150 may continue delivering LV-only pacing 152, e.g., using the adjusted AV delay, monitoring ventricular activations times 154, and evaluating the measured ventricular activation times 150.

Further, although exemplary method 150 is shown for LV-only pacing, it may also be used for patients with right bundle branch block by pacing RV-only and sensing left ventricle activation to determine the AV delay for RV pacing.

Figure 7:
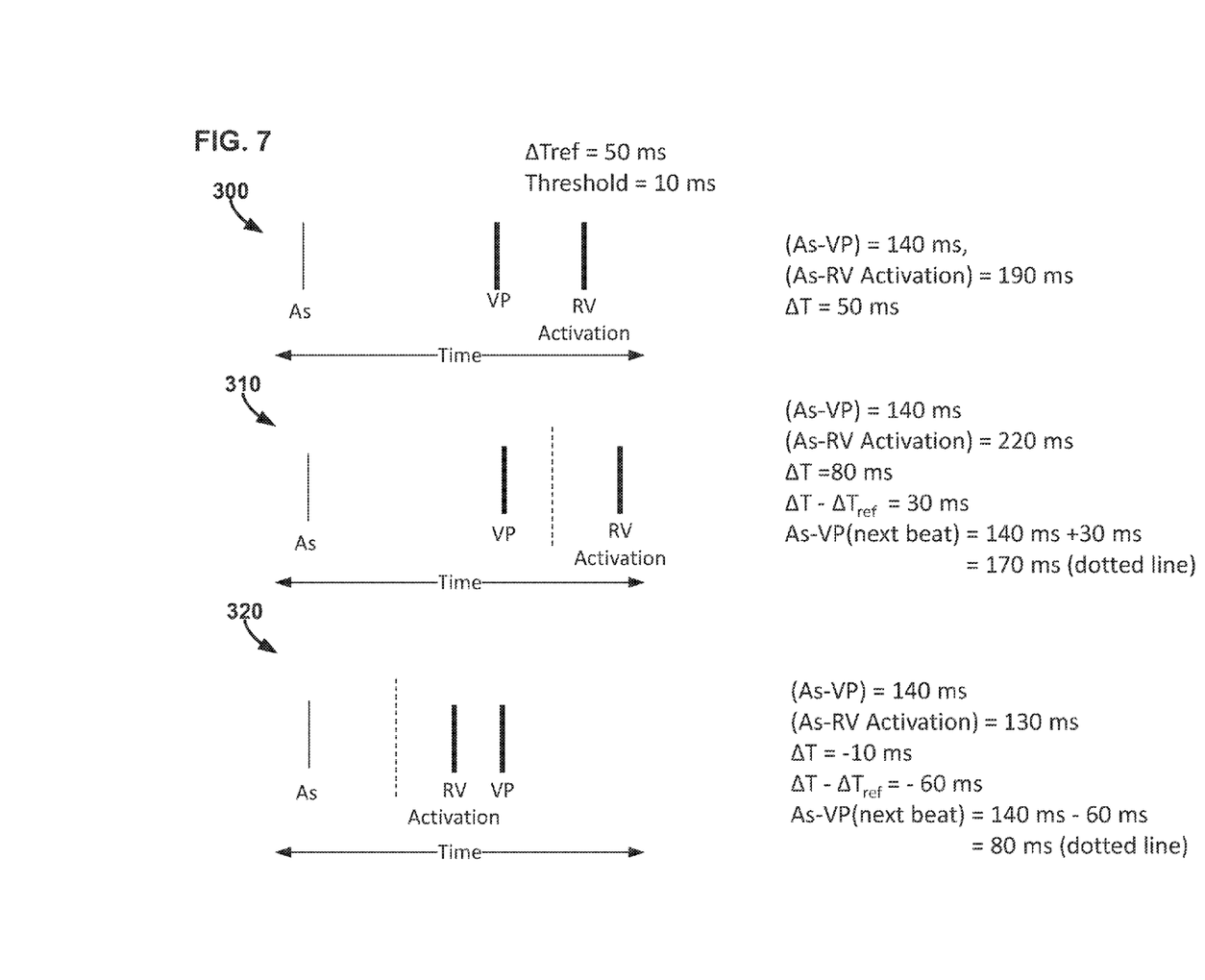
FIG. 7 depicts three exemplary right ventricular activation time calculations.

Three exemplary calculations of measured activation times, or ΔT, are shown in FIG. 7. In these examples, the predetermined reference activation time, or ΔTref, for optimal fusion pacing is 50 ms and the threshold value is 10 ms.

In the first example 300, the time period between an atrial sense (As) and a ventricular pace (VP) is 140 ms (which is the AV delay) and the time period between the atrial sense and a right ventricular activation is 190 ms. Thus, the measured activation time, or ΔT, equals 50 ms, which is within the threshold value, 10 ms, of the predetermined reference activation time of 50 ms. Therefore, no adjustments the AV delay may be triggered or initiated.

In the second example 310, the time period between an atrial sense (As) and a ventricular pace (VP) is 140 ms (which is the AV delay) and the time period between the atrial sense (As) and right ventricular activation is 220 ms. Thus, the measured activation time, or ΔT, equals 80 ms, which is not within the threshold value, 10 ms, of the predetermined reference activation time of 50 ms. Therefore, adjustment of the AV delay may be in initiated.

As shown, the difference between the measured activation time and the predetermined reference activation time may be calculated, which is 30 ms. The AV delay, or As-VP (next beat), may be set to the last AV delay (As-VP), which was 140 ms, plus the difference between the measured activation time and the predetermined reference activation time. As such, the new AV delay may be set to 170 ms. The dotted line in example 310 depicts where the next ventricular pace (VP) should occur using the newly adjusted AV delay.

In the third example 320, the time period between an atrial sense (As) and a ventricular pace (VP) is 140 ms (which is the AV delay) and the time period between the atrial sense (As) and right ventricular activation is 130 ms. In this example, the right ventricular activation occurred before the ventricular pace (VP), and therefore, the right ventricular activation may have occurred naturally (e.g., intrinsic conduction). The measured activation time, or ΔT, equals −10 ms, which is not within the threshold value, 10 ms, of the predetermined reference activation time of 50 ms. Therefore, adjustment of the AV delay may be initiated.

As shown, the difference between the measured activation time and the predetermined reference activation time may be calculated, which is −60 ms. The AV delay, or As-VP (next beat), may be set to the last AV delay (As-VP), which was 140 ms, plus the difference between the measured activation time and the predetermined reference activation time. As such, the new AV delay may be set to 80 ms. The dotted line in example 320 depicts where the next ventricular pace (VP) should occur using the newly adjusted AV delay.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality described to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device operable for delivery of cardiac therapy to a patient, the device comprising:
   a therapy delivery module configured to deliver pacing therapy to the left ventricle of a patient's heart using at least one electrode;
   a sensing module configured to sense electrical activity of the patient's heart using at least one other electrode; and
   a control module coupled to the therapy delivery module and to the sensing module and configured to:
   determine an AV delay;
   control the delivery of pacing therapy to the left ventricle of a patient's heart based on the AV delay, wherein the pacing therapy is delivered over a plurality of heartbeats,
   sense the electrical activity of the patient's heart using the sensing module during the delivery of the pacing therapy,
   measure a ventricular activation time for each of the plurality of heartbeats between the delivery of pacing stimulus of the pacing therapy and at least one selected fiducial point of the sensed electrical activity resulting from at least one of the delivered pacing stimulus of the pacing therapy and an intrinsic conduction of the patient's heart,
   determine between whether or not to modify the AV delay for use in delivering pacing therapy based on one or more of the measured ventricular activation times resulting from the delivered pacing stimulus of the pacing therapy or an intrinsic conduction of the patients' heart being greater than or less than a predetermined reference activation time by a selected threshold value, and
   modify the AV delay for use in delivering pacing therapy based on the measured ventricular activation times when it is determined that the AV delay is to be modified based on the one or more of the measured ventricular activation times being greater than or less than a predetermined reference activation time by a selected threshold value, otherwise not modifying the AV delay based on the determination.

2. The device of claim 1, wherein, to modify the AV delay for use in delivering pacing therapy based on the measured ventricular activation times, the control module is further configured to set the AV delay to the last AV delay plus the last measured activation time minus the predetermined reference activation time.

3. The device of claim 1, wherein, to modify the AV delay for use in delivering pacing therapy based on the measured ventricular activation times, the control module is further configured to set the AV delay to either a mode or a median of a selected number of previous AV delays plus either a mode or median of a selected number of activation time differences, wherein the activation time differences are the measured ventricular activation times minus the predetermined reference activation time.

4. The device of claim 1, wherein the control module is configured to modify the AV delay for use in delivering pacing therapy based on the measured ventricular activation times if a first selected number of the measured ventricular activation times are greater than or less than the predetermined reference activation time by the selected threshold value over a second selected number of heartbeats.

5. The device of claim 1, wherein, to modify the AV delay for use in delivering pacing therapy based on the measured ventricular activation times, the control module is configured to modify the AV delay for use in delivering pacing therapy if a standard deviation of a first selected number of activation time differences are less than a selected variability threshold value over a second selected number of heartbeats, wherein the activation time differences are the measured ventricular activation times minus the predetermined reference activation time.

6. The device of claim 1, wherein the sensing module is configured to sense electrical activity of the right ventricle of the patient's heart using the at least one other electrode, and wherein the control module is configured to sense electrical activity of the right ventricle of the patient's heart using the sensing module during the delivery of the pacing therapy.

7. The device of claim 6, wherein sensing module is further configured to sense near-field electrical activity of the right ventricle of the patient's heart using the at least one other electrode, wherein the control module is configured to sense near-field electrical activity of the right ventricle of the patient's heart using the sensing module during the delivery of the pacing therapy, and wherein the at least one selected fiducial point of the sensed electrical activity comprises a maximum value of the near-field electrical activity of the right ventricle of the patient's heart.

8. The device of claim 7, wherein sensing module is further configured to sense far-field electrical activity of the right ventricle of the patient's heart using the at least one other electrode, wherein the control module is configured to sense far-field electrical activity of the right ventricle of the patient's heart using the sensing module during the delivery of the pacing therapy, and wherein the at least one selected fiducial point of the sensed electrical activity comprises a maximum negative slope of the far-field electrical activity of the right ventricle of the patient's heart.

9. The device of claim 1, wherein the therapy delivery module is further configured to deliver bi-ventricular pacing therapy to the patient's heart, and wherein the control module is further configured to initiate the delivery of bi-ventricular pacing therapy to the patient's heart using the therapy delivery module if the modified AV delay is greater than a selected limit value.

10. The device of claim 1, wherein the control module is configured to deliver left ventricular only pacing therapy to the left ventricle of a patient's heart based on the AV delay and is configured to deliver biventricular pacing to the patient's heart, and wherein the therapy delivery module is further configured to initiate the delivery of bi-ventricular pacing therapy to the patient's heart using the therapy delivery module if the modified AV delay is greater than a selected limit value when delivering left ventricular only pacing therapy to the left ventricle of the patient's heart.

11. A method for use in an implantable medical device operable for delivery of cardiac therapy to a patient, the method comprising:
- delivering pacing therapy to the left ventricle of a patient's heart using at least one electrode based on an AV delay using an implantable medical device, wherein the pacing therapy is delivered over a plurality of heartbeats;
- sensing electrical activity of the patient's heart using at least one other electrode of the implantable medical device during the delivery of the pacing therapy;
- measuring a ventricular activation time for each of the plurality of heartbeats between the delivery of pacing stimulus of the pacing therapy and at least one selected fiducial point of the sensed electrical activity resulting from at least one of the delivered pacing stimulus of the pacing therapy and an intrinsic conduction of the patient's heart;
- determining between whether or not to modify the AV delay for use in delivering pacing therapy based on one or more of the measured ventricular activation times resulting from the delivered pacing stimulus of the pacing therapy or an intrinsic conduction of the patients' heart being greater than or less than a predetermined reference activation time by a selected threshold value; and
- modifying the AV delay for use in delivering pacing therapy based on the measured ventricular activation times when it is determined that the AV delay is to be modified based on the one or more of the measured ventricular activation times being greater than or less than a predetermined reference activation time by a selected threshold value, otherwise not modifying the AV delay based on the determination.

12. The method of claim 11, wherein modifying the AV delay for use in delivering pacing therapy based on the measured ventricular activation times comprises setting the AV delay to the last AV delay plus the last measured ventricular activation time minus the predetermined reference activation time.

13. The method of claim 11, wherein modifying the AV delay for use in delivering pacing therapy based on the measured ventricular activation times comprises setting the AV delay to either a mode or a median of a selected number of previous AV delays plus either a mode or median of the selected number of ventricular activation time differences, wherein the ventricular activation time differences are the measured ventricular activation times minus the predetermined reference activation time.

14. The method of claim 11, wherein modifying the AV delay for use in delivering pacing therapy based on the measured ventricular activation times if a first selected number of the measured ventricular activation times are greater than or less than the predetermined reference activation time by the selected threshold value over a second selected number of heartbeats.

15. The method of claim 11, wherein modifying the AV delay for use in delivering pacing therapy based on the measured ventricular activation times comprises modifying the AV delay for use in delivering pacing therapy if a standard deviation of a first selected number of activation time differences are less than a selected variability threshold value over a second selected number of heartbeats, wherein the ventricular activation time differences are the measured ventricular activation times minus the predetermined reference activation time.

16. The method of claim 11, wherein sensing electrical activity of the patient's heart using at least one other electrode of the implantable medical device during the delivery of the pacing therapy comprises sensing electrical activity of the right ventricle of the patient's heart using the at least one other electrode.

17. The method of claim 16, wherein sensing electrical activity of the patient's heart using at least one other electrode of the implantable medical device during the delivery of the pacing therapy comprises sensing near-field electrical activity of the right ventricle of the patient's heart using the at least one other electrode during the delivery of the pacing therapy, and wherein the at least one selected fiducial point of the sensed electrical activity comprises a maximum value of the near-field electrical activity of the right ventricle of the patient's heart.

18. The method of claim 16, wherein sensing electrical activity of the patient's heart using at least one other electrode of the implantable medical device during the delivery of the pacing therapy comprises sensing far-field electrical activity of the right ventricle of the patient's heart using the at least one other electrode during the delivery of the pacing therapy, and wherein the at least one selected fiducial point of the sensed electrical activity comprises a maximum negative slope of the far-field electrical activity of the right ventricle of the patient's heart.

19. The method of claim 11, wherein the method further comprises delivering bi-ventricular pacing therapy to the patient's heart using the implantable medical device if the modified AV delay is greater than a selected limit value.

20. The method of claim 11, wherein delivering pacing therapy to the left ventricle of a patient's heart comprises delivering left ventricular only pacing therapy to the left ventricle of a patient's heart based on the AV delay, wherein the method further comprises switching from delivering left ventricular only pacing therapy to delivering biventricular pacing to the patient's heart if the modified AV delay is greater than a selected limit value when delivering left ventricular only pacing therapy to the left ventricle of the patient's heart.

* * * * *